United States Patent [19]

Wedemeyer et al.

[11] 4,085,141
[45] Apr. 18, 1978

[54] PROCESS FOR THE PREPARATION OF ANILINES META-SUBSTITUTED BY CHLORINE

[75] Inventors: Karlfried Wedemeyer, Cologne; Wolfgang Kiel, Schildgen; Werner Evertz, Monheim, all of Germany

[73] Assignee: Bayer Aktiengesellschaft, Leverkusen, Germany

[21] Appl. No.: 647,967

[22] Filed: Jan. 9, 1976

[30] Foreign Application Priority Data

Jan. 27, 1975   Germany ............................ 2503187

[51] Int. Cl.$^2$ ...................... C07C 87/50; C07C 87/52; C07C 93/14
[52] U.S. Cl. ............................ 260/570 R; 260/570 D; 260/570.5 CA; 260/570.6; 260/570.7; 260/570.8 R; 260/570.9; 260/571; 260/573; 260/575; 260/578
[58] Field of Search ............... 260/578, 580, 571, 575, 260/570 D, 570 R

[56] References Cited

U.S. PATENT DOCUMENTS

| | | | |
|---|---|---|---|
| 3,888,929 | 6/1975 | Rivier | 260/578 |
| 3,912,783 | 10/1975 | Wedemeyer et al. | 260/620 |
| 4,022,795 | 5/1977 | Bamfield et al. | 260/296 D |

OTHER PUBLICATIONS

Augustine, "Catalytic Hydrogenation", p. 128 (1965).
Handbook of Chemistry and Physics, 52nd Edition, pp. F-183 and F-186, (1971-1972).

*Primary Examiner*—Daniel E. Wyman
*Assistant Examiner*—John J. Doll
*Attorney, Agent, or Firm*—Burgess, Dinklage & Sprung

[57] ABSTRACT

A method of preparing a meta-chloroaniline by contacting a substituted aniline containing a chlorine substituent at other than a meta position and a chlorine substituent at the meta position with hydrogen in solution in an acid medium in the presence of a noble metal catalyst at elevated temperature and pressure. The aniline reactant can contain organo substituents on the ring. The product which results is either a 3-chloroaniline or a 3,5-dichloroaniline which similarly can contain organo substituents on the ring.

30 Claims, No Drawings

PROCESS FOR THE PREPARATION OF ANILINES META-SUBSTITUTED BY CHLORINE

BACKGROUND OF THE INVENTION

1. Field of the Invention

The invention relates to a process for the preparation of anilines meta-substituted by chlorine, by selective dehalogenation of more highly halogenated anilines.

2. Discussion of the Prior Art

It is known to prepare meta-substituted chloroanilines by catalytic hydrogenation of polychloroanilines in the gas phase (DOS (German Published Specification) No. 2,258,769). The polychloroanilines are dehalogenated in a tubular reactor, for example over a copper-(II) chloride/aluminium oxide catalyst, at temperatures aboe 300° C. In the case of the dehalogenation described here, it is always mixtures which are isolated, and these predominantly consist of the starting compound and of compounds which have only been dehalogenated incompletely in the ortho- and para-position. Anilines substituted only in the meta-position by chlorine are only produced in low yields.

SUMMARY OF THE INVENTION

It has been found that anilines which are meta-substituted by chlorine can be prepared when chloroanilines of the formula

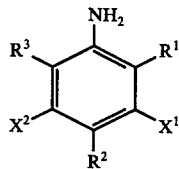

(I)

wherein $X^1$ and $X^2$ are identical or different and represent chlorine, hydrogen or an optionally substituted alkyl, aryl, aralkyl, alkoxy or aralkoxy radical, with one of the radicals $X^1$ or $X^2$ representing chlorine when 3-chloroanilines are being prepared and $X^1$ and $X^2$ representing chlorine when 3,5-dichloroanilines are being prepared and $R^1$, $R^2$ and $R^3$ are identical or different and represent chlorine, hydrogen or an optionally substituted alkyl, aryl, aralkyl, alkoxy or aryloxy radical, with at least one of the radicals $R^1$, $R^2$ or $R^3$ representing chlorine, are reacted with hydrogen in solution in the acid medium in the presence of noble metals which are in the elementary form or in the form of compounds and are optionally applied to supports, at elevated temperature and under pressure.

Using the process according to the invention, meta-substituted anilines of the formula

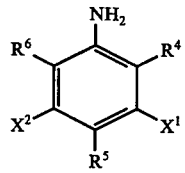

(II)

wherein $X^1$ and $X^2$ have the abovementioned meaning and $R^4$, $R^5$ and $R^6$ are identical or different and represent hydrogen or an optionally substituted alkyl, aryl, aralkyl, alkoxy or aryloxy radical are generally obtained.

Optionally substituted aliphatic radicals ($R^1$, $R^2$, $R^3$, $R^4$, $R^5$ and $R^6$ can be, for example, straight-chain or branched aliphatic radicals with 1 to 12, preferably with 1 to 6, carbon atoms, and cycloaliphatic radicals with 5 to 8, preferably 5 and 6, carbon atoms in the ring. The methyl, ethyl, propyl, isopropyl, butyl, pentyl, hexyl, octyl, nonyl, decyl, dodecyl, cyclopentyl, cyclohexyl, cycloheptyl and cyclooctyl radical may be mentioned as examples.

Optionally substituted aromatic radicals $R^1$, $R^2$, $R^3$, $R^4$, $R^5$ and $R^6$ can denote radicals of $C_6$ to $C_{12}$ aryl groups especially members from the benzene series, preferably the phenyl radical or the naphthyl radical.

Optionally substituted aralkyl radicals $R^1$, $R^2$, $R^3$, $R^4$, $R^5$ and $R^6$ can be, for example, radicals with 7 to 18 carbon atoms, of which the aliphatic part contains 1 to 6 carbon atoms, preferably 1 to 3 carbon atoms, and of which the aromatic part represents a radical of the benzene series, preferably the phenyl or naphthyl radical. The following aralkyl radicals may be mentioned as examples: the benzyl, m-ethylphenyl, γ-propylphenyl, β-phenyl-n-hexyl, β-[naphthyl-(1)]-ethyl, ω-butylphenyl, ω-pentylphenyl and ω-hexylphenyl radical.

Optionally substituted alkoxy radicals $R^1$, $R^2$, $R^3$, $R^4$, $R^5$ and $R^6$ can be either straight-chain and branched radicals with 1 to 12, preferably with 1 to 6, carbon atoms, or cycloaliphatic radicals with 5 and 6 carbon atoms in the ring. The methoxy, ethoxy, propoxy, isopropoxy, butoxy, tert.-butoxy, pentoxy, hexoxy, octoxy, nonoxy, decoxy, do-decoxy, cyclopentoxy and cyclohexoxy radical may be mentioned as examples.

Radicals of the benzene series, preferably the phenoxy radical, may be mentioned as optionally substituted aryloxy radicals $R^1$, $R^2$, $R^3$, $R^4$, $R^5$ and $R^6$.

Possible substituents of the abovementioned alkyl, aryl, aralkyl, alkoxy or aralkoxy radicals are, for example, the amino group, the hydroxyl group, straight-chain or branched alkyl radicals with up to 12, preferably with up to 6, carbon atoms, cycloaliphatic radicals, preferably with 5 and 6 carbon atoms in the ring, and aryl radicals, preferably the phenyl radical.

Particularly preferred chloroanilines which can be employed for the process according to the invention are compounds of the formula

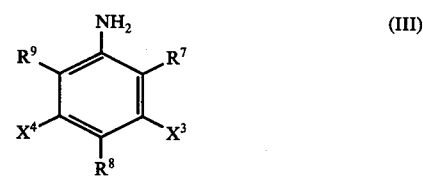

(III)

wherein $X^3$ $X^4$ are identical or different and represent chlorine or hydrogen, with one of the radicals $X^3$ or $X^4$ representing chlorine when 3-chloroanilines are being prepared and $X^3$ and $X^4$ representing chlorine when 3,5-dichloroanilines are being prepared, and $R^7$, $R^8$ and $R^9$ are identical or different and represent chlorine, hydrogen, the methyl or phenyl group or the radical

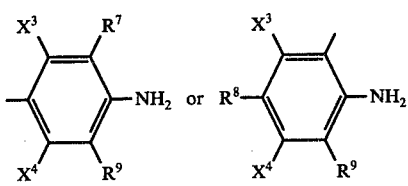

with at least one of the radicals $R^7$, $R^8$ or $R^9$ representing chlorine.

The polychloroanilines of the formula I which can be used for the process according to the invention are known and easily accessible.

Examples which may be mentioned are 2,3-dichloroaniline, 2,5-dichloroaniline, 3,4-dichloroaniline, 2,3,4-trichloroaniline, 2,3,5-trichloroaniline, 2,4,5-trichloroaniline, 2,3,6-trichloroaniline, 3,4,5-trichloroaniline, 2,3,4,6-tetrachloroaniline, 2,3,4,5-tetrachloroaniline, 2,3,5,6-tetrachloroaniline, pentachloroaniline, 4,5,6-trichloro-2-methylaniline, 2,5-dichloro-4-methylaniline, 2,3,5,6-tetrachloro-4-methylaniline, 2,5-dichloro-3,4-dimethylaniline, 2,5-dichloro-4-ethylaniline, 2,5-dichloro-4-propylaniline, 3,4,6-trichloro-2-benzylaniline, 2,2′-diamino-3,5,6,3′,5′,6′-hexachlorodiphenylmethane, 3,4,5-trichloro-2-aminodiphenyl, 4,4′-diaminooctachlorodiphenyl, 3,4-dichloro-2-methoxyaniline, 3,6-dichloro-2-methoxyaniline, 4,5-dichloro-2-methoxyaniline, 5,6-dichloro-2-methoxyaniline, 3,4,6-trichloro-2-methoxyaniline, 3,4,5-trichloro-2-methoxyaniline, 3,4,5,6-tetrachloro-2-methoxyaniline, 4,5-dichloro-3-methoxyaniline, 5,6-dichloro-3-methoxyaniline, 2,5-dichloro-3-methoxyaniline, 4,5,6-trichloro-3-methoxyaniline, 2,4,5,6-tetrachloro-3-methoxyaniline, 2,3-dichloro-4-methoxyaniline, 2,5-dichloro-4-methoxyaniline, 2,3,6-trichloro-4-methoxyaniline, 2,3,5-trichloro-4-methoxyaniline, 2,3,5,6-tetrachloro-4-methoxyaniline, 4,5-dichloro-2-phenoxyaniline, 3,4,5,6-tetrachloro-2-phenoxyaniline, 2,4,5,6-tetrachloro-3-phenoxyaniline, 2,5-dichloro-4-phenoxyaniline and 2,3,5,6-tetrachloro-4-phenoxyaniline.

The process according to the invention is carried out in the presence of a catalyst of noble metals in the elementary form or in the form of compounds.

Noble metals which may be mentioned are the elements of group VIII of the periodic table, such as ruthenium, rhodium, palladium, osmium, iridium and platinum, preferably palladium and platinum. The oxides, sulphides and/or polysulphides are examples of compounds of noble metals which can be employed.

The catalysts according to the process of the invention can of course also be used on supports. For this purpose, all supports which are in themselves known can be used, provided they are inert to water and acids. Examples of such supports which may be mentioned are barium sulphate and active charcoal, preferably active charcoal.

The noble metal catalyst on a support can be prepared in a manner which is in itself known. For example, the support is suspended in the aqueous solution of the noble metal and the noble metal is then precipitated on the support by adding a reducing agent, such as, for example, hydrogen or hydrazine.

Particularly when carrying out the process according to the invention continuously, it is advantageous to arrange the noble metal catalyst on a support, as a fixed bed or fluidised bed catalyst in the reaction chamber.

The catalysts which are employed for carrying out the process according to the invention retain their activity and their selectivity over a long period even if re-used repeatedly or if the process according to the invention is carried out continuously, and give constant high yields.

The amount of catalyst which is employed for carrying out the process according to the invention is not critical and can be varied within wide limits. In general, 0.1 to 2% by weight, preferably 1 to 1.5% by weight, relative to the chloroaniline used as the starting material, are employed. If a catalyst applied to a support is used, a correspondingly larger amount of supported catalyst is employed; in general, 1 to 20% by weight, preferably 10 to 15% by weight, relative to the starting material, are then employed.

The process according to the invention is carried out in solution. Solvents which can be used are all protic and aprotic solvents which are inert under the reaction conditions.

Examples of protic solvents which may be mentioned are water, methyl alcohol and ethyl alcohol, preferably water.

Examples of aprotic solvents which may be mentioned are benzene, toluene and xylene, preferably toluene. If an aprotic solvent is used, the process is preferably carried out under anhydrous conditions. In that case it is of course also necessary that the catalyst should be employed dry.

The process according to the invention is carried out in an acid medium.

All inorganic and organic acids can be used as the acids. Inorganic mineral acids which should be mentioned are hydrochloric acid, sulphuric acid and phosphoric acid, preferably hydrochloric acid and sulphuric acid, and organic acids which should be mentioned are acetic acid and propionic acid, preferably acetic acid.

Particularly for the preparation of 3,5-dichloroanilines, it can be advantageous to use a mixture of the abovementioned acids. Preferably, a mixture of hydrochloric acid and sulphuric acid is employed for this purpose.

Whilst the amount of acid employed can be varied within wide limits without adversely affecting the outcome of the reaction, the amount used should not be less than 0.1 mol of acid per mol of aniline. To carry out the reaction under optimum conditions it is expedient specifically to determine the suitable amount of acid. It depends on the nature of the acid and on the starting compounds. In general it is advantageous to carry out the reactions in an aqueous hydrochloric acid, optionally with addition of 1 to 10% by weight of concentrated sulphuric acid, relative to the total amount of solvent. The amount of hydrochloric acid is so chosen as to give a molar excess relative to the starting product employed. It is also advantageous to carry out the reaction in a toluene/sulphuric acid solution, in which case the sulphuric acid added can be between 0.5 and 20% by weight, relative to the solvent, depending on the nature and amount of the polychloroaniline employed.

If the process according to the invention is carried out in an aqueous solution, it is generally carried out at a pH value of less than 4, preferably less than 1.

The process according to the invention can be illustrated by the following equations for the dechlorination of pentachloroaniline to 3,5-dichloroaniline:

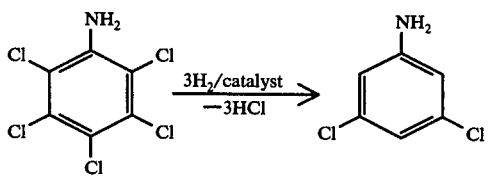

In general, the process is carried out by initially introducing the starting material, solvent, acid and catalyst into an acid-resistant autoclave and, after sealing the autoclave, displacing the air with nitrogen and then displacing the nitrogen with hydrogen.

To carry out the reaction, the gaseous hydrogen is passed into the reaction mixture. In general, the reaction is carried out at a hydrogen pressure of 20 to 200 atmospheres gauge, preferably of 40 to 150 atmospheres gauge, and particularly preferentially of 60 to 120 atmospheres gauge.

In general, the process according to the invention is carried out at a temperature of 100° to 350° C, preferably of 150° to 300° C and particularly preferentially of 180° to 270° C.

Since the rate of reaction increases at higher temperatures, it is not possible to specify the reaction time in general terms. However, if the time which would be required for a conversion is exceeded, neither the selectivity of the dechlorination nor the yield are adversely effected.

After completion of the reaction the catalyst is filtered off hot if water is used as the solvent. The 3-chloroanilines or 3,5-dichloroanilines are liberated by adding an alkali metal hydroxide, for example sodium hydroxide, and are extracted with the water-immiscible solvent, for example methylene chloride. The chloroanilines can be obtained from the solvent by, for example, distillation.

If a solvent which is immiscible with water is employed in the reaction, the 3-chloroanilines or 3,5-dichloroanilines can be liberated by adding aqueous alkali metal hydroxide. Thereafter the solvent can be separated off and the chloroaniline isolated by, for example, distillation.

The process according to the invention can be carried out either discontinuously or continuously.

The process according to the invention has the advantage that by selective dechlorination of higher chlorinated anilines it is possible to prepare anilines which are meta-substituted by chlorine, in a simple manner and with high yields. Above all the anilines substituted by chlorine in both meta-positions, such as, for example, 3,5-dichloroaniline, can only be synthesised in a very labour-intensive and cost-intensive manner if previously known processes of preparation are used. For example, the previously customary preparation of 3,5-dichloroaniline is via the chlorination of p-nitroaniline to 1-amino-2,6-dichloro-4-nitrobenzene. The amino group is then diazotised and reductively replaced by hydrogen. The resulting 3,5-dichloronitrobenzene is then reduced to 3,5-dichloroaniline (Ber. dtsch. chem. Ges. 8, 143 and 145).

A further advantage of the process according to the invention is that chloroaniline mixtures which can only be separated with difficulty and which contain, in addition to the polychloroanilines substituted in the m-position relative to the amino group by chlorine, further chloroanilines or polychloroanilines in which there is no chlorine in the m-position relative to the amino group, can also be used as the starting material. These compounds are dechlorinated to aniline by the process according to the invention and the aniline can easily be separated off by distillation. In contrast, the separation of a polychloroaniline mixture is involved and lengthy.

The following may be mentioned as examples of chloroanilines of the formula II which are meta-substituted by chlorine and which can be prepared according to the process of the invention: 3-chloroaniline, 3,5-dichloroaniline, 5-chloro-2-methylaniline, 5-chloro-3-methylaniline, 3-chloro-4-methylaniline, 3,5-dichloro-4-methylaniline, 5-chloro-3,4-dimethylaniline, 3-chloro-4-ethylaniline, 3-chloro-2-benzylaniline, 4,4'-diamino-2,6,2',6'-tetrachlorodiphenyl, 3-chloro-2-methoxyaniline, 5-chloro-2-methoxyaniline, 3,5-dichloro-2-methoxyaniline, 3-chloro-4-methoxyaniline, 5-chloro-3-methoxyaniline, 3,5-dichloro-4-methoxyaniline, 3-chloro-2-phenoxyaniline, 5-chloro-2-phenoxyaniline, 3,5-dichloro-2-phenoxyaniline and 3,5-dichloro-4-phenoxyaniline.

The 3-chloroanilines and 3,5-dichloroanilines obtainable according to the process of the invention are known intermediate products and can be used for the preparation of plant protection agents (German Patent Specification No. 1,034,912, DOS (German Published Specification) No. 2,021,327, DOS (German Published Specification) No. 1,812,206, DOS (German Published Specification) No. 1,958,183, U.S. Pat. No. 2,906,614, U.S. Pat. No. 2,655,445 and U.S. Pat. No. 3,652,737).

EXAMPLE 1

Preparation of 3-chloroaniline in aqueous solution 40.5 g (0.25 mol) of 2,5-dichloroaniline, 250 ml of 36% strength aqueous hydrochloric acid and 5 g of a 5% strength palladium/active charcoal catalyst are initially introduced into an 0.7 l autoclave made of tantalum. The autoclave is flushed first with nitrogen and then with hydrogen. The dechlorination is carried out over the course of 30 minutes at 220° C and a hydrogen pressure of 100 atmospheres gauge. The catalyst is separated off by filtration and is washed twice with hot water. The reaction solution, together with the wash water, is rendered alkaline and warmed. After cooling, the reaction product is extracted twice with 150 ml of methylene chloride. After distilling off the methylene chloride, and a subsequent fractional distillation, 31.3 g of 3-chloroaniline (yield: 98.7% of theory) are obtained.

EXAMPLE 2

Preparation of 3-chloroaniline in toluene 40.5 g (0.25 mol) of 2,5-dichloroaniline, 250 ml of toluene, 2 ml of concentrated sulphuric acid and 5 g of a 5% strength palladium/active charcoal catalyst are initially introduced into an 0.7 l autoclave made of tantalum. The autoclave is flushed first with nitrogen and then with hydrogen. The dechlorination is carried out over the course of 90 minutes at 250° C and a hydrogen pressure of 200 atmospheres gauge. 300 ml of hot water are added to the reaction mixture and the whole is warmed. The catalyst is filtered off and washed twice with hot water. The reaction solution, together with the wash water, is rendered alkaline and warmed. After cooling, the toluene phase is separated off and the aqueous phase is extracted twice more with 100 ml of toluene. After distilling off the toluene, and subsequent fractional distillation, 28.8 g of 3-chloroaniline (yield: 90.6% of theory) are obtained.

EXAMPLE 3

Preparation of 3,5-dichloroaniline 57.7 g (0.25 mol) of 2,3,5,6-tetrachloroaniline, 250 ml of 36% strength aqueous solution of hydrochloric acid, 5 ml of concentrated sulphuric acid and 5 g of a 5% strength palladium/active charcoal catalyst are introduced into an 0.7 l autoclave made of tantalum. The autoclave is flushed first with nitrogen and then with hydrogen. The dechlorination is carried out over the course of 2 hours at 250° C and a hydrogen pressure of 200 atmospheres gauge. After the reaction, the catalyst is filtered off and washed twice with hot water. The reaction solution together with the wash water is rendered alkaline and warmed. After cooling, the reaction product is extracted twice with 150 ml of methylene chloride. After distilling off the methylene chloride, and subsequent fractional distillation, 36 g of 3,5-dichloroaniline (yield: 89% of theory) are obtained.

EXAMPLE 4

Preparation of 3,5-dichloroaniline from pentachloroaniline 66.2 g (0.25 mol) of pentachloroaniline, 250 ml of a 36% strength aqueous solution of hydrochloric acid, 5 ml of concentrated sulphuric acid and 5 g of a 5% strength palladium/active charcoal catalyst are introduced into an 0.7 l autoclave made of tantalum. The autoclave is flushed first with nitrogen and then with hydrogen. The dechlorination is carried out over the course of 2 hours at 250° C and a hydrogen pressure of 200 atmospheres gauge. After the reaction is complete, the catalyst is filtered off and washed twice with hot water. The reaction solution together with the wash water is rendered alkaline and warmed. After cooling, the reaction product is extracted twice with 150 ml of methylene chloride. After distilling off the methylene chloride, and subsequent fractional distillation, 29.6 g of 3,5-dichloroaniline (yield: 73% of theory), of 95% purity, are obtained.

EXAMPLE 5

3,5-Dichloro-4-methylaniline from 2,3,5,6-tetrachloro-4-methylaniline 61.1 g (0.25 mol) of 2,3,5,6-tetrachloro-4-methylaniline, 250 ml of a 36% strength aqueous solution of hydrochloric acid, 2 g of concentrated sulphuric acid and 5 g of a 5% strength palladium/active charcoal catalyst are initially introduced into an 0.7 l autoclave made of tantalum. The autoclave is flushed first with nitrogen and then with hydrogen. The dechlorination is carried out over the course of 2 hours at 250° C and a hydrogen pressure of 200 atmospheres gauge. After the reaction, the catalyst is filtered off and washed twice with hot water. The reaction solution together with the wash water is rendered alkaline and warmed. After cooling, the reaction product is extracted twice with 150 ml of methylene chloride. After distilling off the methylene chloride and subsequent fractional distillation, 38.2 g of 3,5-dichloro-4-methylaniline (yield 87% of theory) of 95% purity are obtained.

What is claimed is:

1. A process for the preparation of a chlorine meta-substituted aniline of the formula

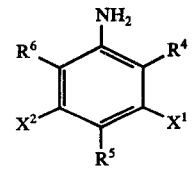

wherein
X$^1$ and X$^2$ are identical or different and represent chlorine, hydrogen or an optionally substituted alkyl, aryl, aralkyl, alkoxy or aralkoxy radical, at least one of said radicals X$^1$ or X$^2$ being chlorine;
R$^4$, R$^5$ and R$^6$ each independently being hydrogen or an optionally substituted alkyl, aryl, aralkyl, alkoxy or aryloxy radical which comprises contacting a chloroaniline of the formula

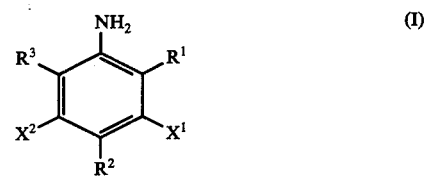

wherein
X$^1$ and X$^2$ have the previously assigned significance;
R$^1$, R$^2$ and R$^3$ are each independently chlorine, hydrogen or an optionally substituted alkyl, aryl, aralkyl, alkoxy or aryloxy, at least one of said R$^1$, R$^2$ or R$^3$ members being chlorine, with hydrogen in a solution in an acid medium in the presence of a noble metal.

2. A process according to claim 1 wherein the noble metal is in elementary form.

3. A process according to claim 1 wherein the noble metal is in the form of a noble metal compound.

4. A process according to claim 1 wherein the process is carried out at a temperature of 150° to 350° C.

5. A process according to claim 4 wherein the process is carried out at a temperature of 180° to 270° C.

6. A process according to claim 1 wherein the process is carried out under hydrogen pressure of 20 to 200 atmospheres gauge.

7. A process according to claim 6 wherein the process is carried out under hydrogen pressure of 60 to 120 atmospheres gauge.

8. A process according to claim 1 wherein at least one of said R$^4$, R$^5$ or R$^6$ has the formula

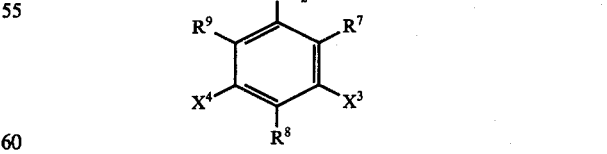

wherein
X$^3$ and X$^4$ are each independently chlorine, hydrogen or an optionally substituted alkyl, aryl, aralkyl, alkoxy or aryloxy radical, with at least one of said X$^3$ and X$^4$ being chlorine;
R$^7$, R$^8$ and R$^9$ are each independently chlorine, hydrogen, methyl, phenyl or a radical of the formula

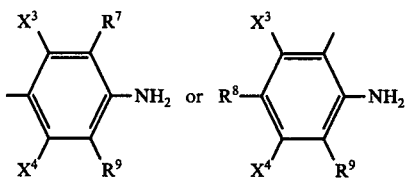

wherein at least one of said radicals $R^7$, $R^8$ or $R^9$ is chlorine.

9. A process according to claim 1 wherein said noble metal is an element of Group VIII of the Periodic Table and said noble metal is in an elementary form or in the form of an oxide or sulfide.

10. A process according to claim 9 wherein said noble metal is platinum or palladium.

11. A process according to claim 1 wherein said noble metal is disposed on a support of active charcoal 12. A process according to claim 1 carried out in a protic solvent.

13. A process according to claim 1 carried out in an aprotic solvent.

14. A process according to claim 1 wherein the acid of the acid medium is hydrochloric acid and said process is carried out in aqueous medium.

15. A process according to claim 1 wherein said process is carried out in toluene containing sulfuric acid.

16. A process according to claim 1 wherein said process is carried out in aqueous medium containing hydrochloric acid and sulfuric acid.

17. A process according to claim 1 wherein at least one of said $R^1$, $R^2$, $R^3$, $R^4$, $R^5$, $R^6$ is a straight chain or branched aliphatic radical having 1 to 12 carbon atoms, a cycloaliphatic radical having from 5 to 8 carbon atoms, an aryl group having between 6 and 12 carbon atoms in the ring, an aralkyl radical of 6 to 12 carbon atoms in the aryl group and 1 to 6 carbon atoms in the aliphatic portion, or an alkoxy group having 1 to 12 straight chain or branched chain carbon atoms.

18. A process according to claim 17 wherein at least one of said $R^1$, $R^2$, $R^3$, $R^4$, $R^5$, $R^6$ is an aliphatic radical having 1 to 6 carbon atoms therein, a cycloaliphatic radical having 5 to 6 carbon atoms therein, a phenyl or naphthyl radical, an aralkyl radical of a phenyl or naphthyl radical containing between 1 and 3 carbon atoms in the aliphatic portion, or an alkoxy group having 1 to 6 carbon atoms therein.

19. A process according to claim 18 wherein at least one of said $R^1$, $R^2$, $R^3$, $R^4$, $R^5$, $R^6$ is selected from the group consisting of methyl, ethyl, propyl, isopropyl, butyl, pentyl, hexyl, octyl, nonyl, decyl, dodecyl, cyclopentyl, cyclohexyl, cycloheptyl, cyclooctyl, phenyl, naphthyl, benzyl, m-ethylphenyl, γ-propylphenyl, β-phenyl-n-hexyl, β-[naphthyl (1)]-ethyl, ω-butylphenyl, ω-pentyl-phenyl, ω-hexylphenyl, methoxy, ethoxy, propoxy, isopropoxy, butoxy, tert.-butoxy, pentoxy, hexoxy, octoxy, nonoxy, decoxy, dodecoxy, cyclopentoxy or cyclohexoxy.

20. A process according to claim 19 wherein at least one of said substituents $R^1$, $R^2$, $R^3$, $R^4$, $R^5$, $R^6$ is substituted by an amine group, a hydroxyl group, a straight or branched chain alkyl radical of up to 12 carbon atoms, a cycloaliphatic radical having 5 to 6 carbon atoms or an aryl radical.

21. A process according to claim 1 wherein the chloroaniline reactant is selected from the group consisting of of 2,3-dichloroaniline, 2,5-dichloroaniline, 3,4-dichloroaniline, 2,3,4-trichloroaniline, 2,3,5-trichloroaniline,2,4,5-trichloroaniline, 2,3,6-trichloroaniline, 3,4,5-trichloroaniline, 2,3,4,6-tetrachloroaniline, 2,3,4,5-tetrachloroaniline, 2,3,5,6-tetrachloroaniline, pentachloroaniline, 4,5,6-trichloro- 2-methylaniline, 2,5-dichloro-4-methylaniline, 2,3,5,6-tetrachloro-4-methylaniline, 2,5-dichloro-3,4-dimethylaniline, 2,5-dichloro-4-ethylaniline, 2,5-dichloro-4-propylaniline, 3,4,6-trichloro-2-benzylaniline, 2,2'-diamino-3,5,6,3',5',6'-hexachlorodiphenylmethane, 3,4,5-trichloro-2-aminodiphenyl, 4,4'-diaminooctachlorodiphenyl, 3,4-dichloro-2-methoxyaniline, 3,6-dichloro-2-methoxyaniline, 4,5-dichloro-2-methoxyaniline, 5,6-dichloro-2-methoxyaniline, 3,4,6-trichloro-2-methoxyaniline, 3,4,5-trichloro-2-methoxyaniline, 3,4,5,6-tetrachloro-2-methoxyaniline, 4,5-dichloro-3-methoxyaniline, 5,6-dichloro-3-methoxyaniline, 2,5-dichloro-3-methoxyaniline, 4,5,6-trichloro-3-methoxyaniline, 2,4,5,6-tetrachloro-3-methoxyaniline, 2,3-dichloro-4-methoxyaniline, 2,5-dichloro-4-methoxyaniline, 2,3,6-trichloro-4-methoxyaniline, 2,3,5-trichloro-4-methoxyaniline, 2,3,5,6-tetrachloro-4-methoxyaniline, 4,5-dichloro-2-phenoxyaniline, 3,4,5,6-tetrachloro-2-phenoxyaniline, 2,4,5,6-tetrachloro-3-phenoxyaniline, 2,5-dichloro-4-phenoxyaniline and 2,3,5,6-tetrachloro-4-phenoxyaniline.

22. A process according to claim 1 wherein said noble metal is selected from the group consisting of ruthenium, rhodium, palladium, osmium, iridium and platinum.

23. A process according to claim 1 wherein the acid of the acid medium is selected from the group consisting of hydrochloric acid, sulfuric acid, phosphoric acid, acetic acid and propionic acid.

24. A process according to claim 1 wherein the acid of the acid medium is present in an amount not less than 0.1 mol of acid per mol of aniline reactant.

25. A process according to claim 1 wherein the process is carried out in aqueous solution whose pH has a value less than 4.

26. A process according to claim 25 wherein the pH of the aqueous solution is less than 1.

27. A process according to claim 1 wherein $R_4$, $R_5$ and $R_6$ are independently hydrogen or an optionally substituted alkyl, aryl or aralkyl group and $X^1$ and $X^2$ are independently chlorine, hydrogen or an optionally substituted alkyl, aryl or aralkyl group.

28. A process according to claim 27 wherein one of said $X^1$ and $X^2$ is hydrogen.

29. A process according to claim 27 wherein $R_4$, $R_5$ and $R_6$ are hydrogen.

30. A process according to claim 29 wherein one of said $X^1$ and $X^2$ is hydrogen.

* * * * *